US008030360B2

(12) United States Patent
Shudo et al.

(10) Patent No.: US 8,030,360 B2
(45) Date of Patent: Oct. 4, 2011

(54) ANTI-WRINKLE AGENT

(75) Inventors: Koichi Shudo, Tokyo (JP); Seishiro Fujii, Zama (JP)

(73) Assignee: Kemphys Ltd., Tokyo (JP)

( * ) Notice: Subject to any disclaimer, the term of this patent is extended or adjusted under 35 U.S.C. 154(b) by 0 days.

(21) Appl. No.: 12/040,374

(22) Filed: Feb. 29, 2008

(65) Prior Publication Data

US 2008/0153781 A1 Jun. 26, 2008

Related U.S. Application Data

(62) Division of application No. 10/932,097, filed on Sep. 2, 2004, now abandoned.

(30) Foreign Application Priority Data

Mar. 11, 2004 (JP) ................................. 2004-068454

(51) Int. Cl.
A61K 31/07 (2006.01)
A61K 8/00 (2006.01)
(52) U.S. Cl. ........................................ 514/725; 424/401
(58) Field of Classification Search .................. 514/725; 424/401
See application file for complete search history.

(56) References Cited

U.S. PATENT DOCUMENTS

| 3,932,665 A | 1/1976 | Van Scott et al. |
|---|---|---|
| 4,703,110 A | 10/1987 | Shudo |
| 4,808,631 A | 2/1989 | Klaus |
| 4,934,114 A | 6/1990 | Lindsey |
| 5,081,271 A | 1/1992 | Shudo |
| 5,155,249 A | 10/1992 | Shudo |
| 5,216,148 A | 6/1993 | Klaus et al. |
| 5,750,515 A | 5/1998 | Shibata et al. |
| 5,807,890 A | 9/1998 | Yu et al. |
| 5,807,900 A | 9/1998 | Bryce et al. |
| 6,004,987 A | 12/1999 | Demarchez et al. |
| 7,126,017 B2 * | 10/2006 | DeLuca et al. ................ 554/167 |
| 2001/0018456 A1 | 8/2001 | Fesus et al. |
| 2001/0053347 A1 | 12/2001 | Varani et al. |
| 2004/0167215 A1 | 8/2004 | DeLuca et al. |
| 2005/0085539 A1 | 4/2005 | DeLuca et al. |

FOREIGN PATENT DOCUMENTS

| EP | 0269899 | 6/1988 |
|---|---|---|
| EP | 379367 | 7/1990 |
| EP | 0379367 | 7/1990 |
| EP | 0391033 | 10/1990 |
| JP | 61-22047 | 4/1986 |
| JP | 61-076440 | 4/1986 |
| JP | 1-249783 | 10/1989 |
| JP | 2-247185 | 10/1990 |
| JP | 2-288822 | 11/1990 |
| JP | 7-165709 | 6/1995 |
| JP | 9-2972 | 1/1997 |
| JP | 11-501661 | 2/1999 |
| JP | 2000-511558 | 9/2000 |
| WO | 96/30009 | 10/1996 |
| WO | 97/13505 | 4/1997 |
| WO | 97/48672 | 12/1997 |
| WO | 2004/065358 | 8/2004 |

OTHER PUBLICATIONS

Poucher's Perfumes, Cosmetics and Soaps, 2000, Kluwer Academic Publishers, (10th ed. By Hilda Butler), pp. 403-405.*
English language Abstract of JP 11-501661, 1999.
English language Abstract of JP 61-076440, 1986.
Mizojiri et al., Arzneim.-Forsch/Drug Res. 47 (I), Nr. 3 (1997), pp. 270-27.
Edwards et al., Prog. Med. 1996, vol. 16, pp. 1321-1341.
Shuto et al., Journal of Japanese Cosmetic Science Society, 1992, vol. 16, No. 3, pp. 172-174.
Griffiths, Clinical and Experimental Dermatology, vol. 24, No. 4, Jul. 1999, pp. 329-335, XP002447120.
Albert M. Kligman, "Current Status of Topical Tretinoin in the Treatment of Photoaged Skin", Drugs & Aging, vol. 2, No. 1, pp. 7-13 (1992).
Michael B. Sporn et al., "Chapter 5: Biological Methods for Analysis and Assay of Retinoids—Relationships Between Structure and Activity", The Retinoids, vol. 1, Academic Press, Inc., pp. 235-279 (1984).
Hugues de The, Anne Dejean, "The Retinoic Acid Receptors", Saurat J-H (ed): Retinoids: 10 Years on. Basel, Karger, pp. 2-9 (1991).
Hiroyuki Kagechika et al., "Retinobenzoic Acids. 2. Structure-Activity Relationships of Chalcone-4-carboxylic Acids and Flavone-4'-carboxylic Acids", ournal of Medicinal Chemistry, vol. 32, pp. 835-840 (1989).
Takeru Yamakawa et al., "Retinobenzoic Acids. 5. Retinoidal Activities of Compounds Having Trimethylsilyl or Trimethylgermyl Group(s) in Human Promyelocytic Leukemia Cells HL-60", Journal of Medicinal Chemistry, vol. 33, pp. 1430-1437 (1990).
Yuichi Hashimoto, "Retinobenzoic Acids and Nuclear Retinoic Acid Receptors", Cell Structure and Function, vol. 16, pp. 113-123 (1991).
Yuichi Hashimoto et al, "Expression of Retinoic Acid Receptor Genes and the Ligand-Binding Selectivity of Retinoic Acid Receptors (RAR'S)" Biochemical and Biophysical Research Communications, vol. 166, No. 3, pp. 1300-1307 (1990).
English language Abstract of JP09-002972, 1997.
English language Abstract of JP 2-247185, 1990.
English language Abstract of JP 2-288822, 1990.
English language Abstract of JP 7-165709, 1995.
English language Abstract of JP 2000-511558, 2000.
English language Abstract of JP 1-249783, 1989.
English language Abstract of JP 61-22047, 1986.
Flick, E., Cosmetic and Toiletry Formulations, 1989, Noyes Publications, 2nd Ed., vol. 1., p. 276.
Takayoshi Tadali, 1993, vol. 88, No. 3, pp. 277-288.
Keiichi Ueda, 1995, vol. 90 No. 3, pp. 345-354.

* cited by examiner

Primary Examiner — Gina C Yu
(74) Attorney, Agent, or Firm — Greenblum & Bernstein, P.L.C.

(57) ABSTRACT

A medicament having an anti-wrinkle action, which comprises as an active ingredient a retinoid having a fundamental structure of a phenyl substituted carbamoyl benzoic acid or a phenyl substituted carboxamide benzoic acid (for example, 4-(3,5-bis(trimethylsilyl)phenylcarboxamide) benzoic acid, 4-[(5,6,7,8-tetrahydro-5,5,8,8-tetramethyl-2-naphthalenyl) carbamoyl]benzoic acid, or the like).

2 Claims, 6 Drawing Sheets

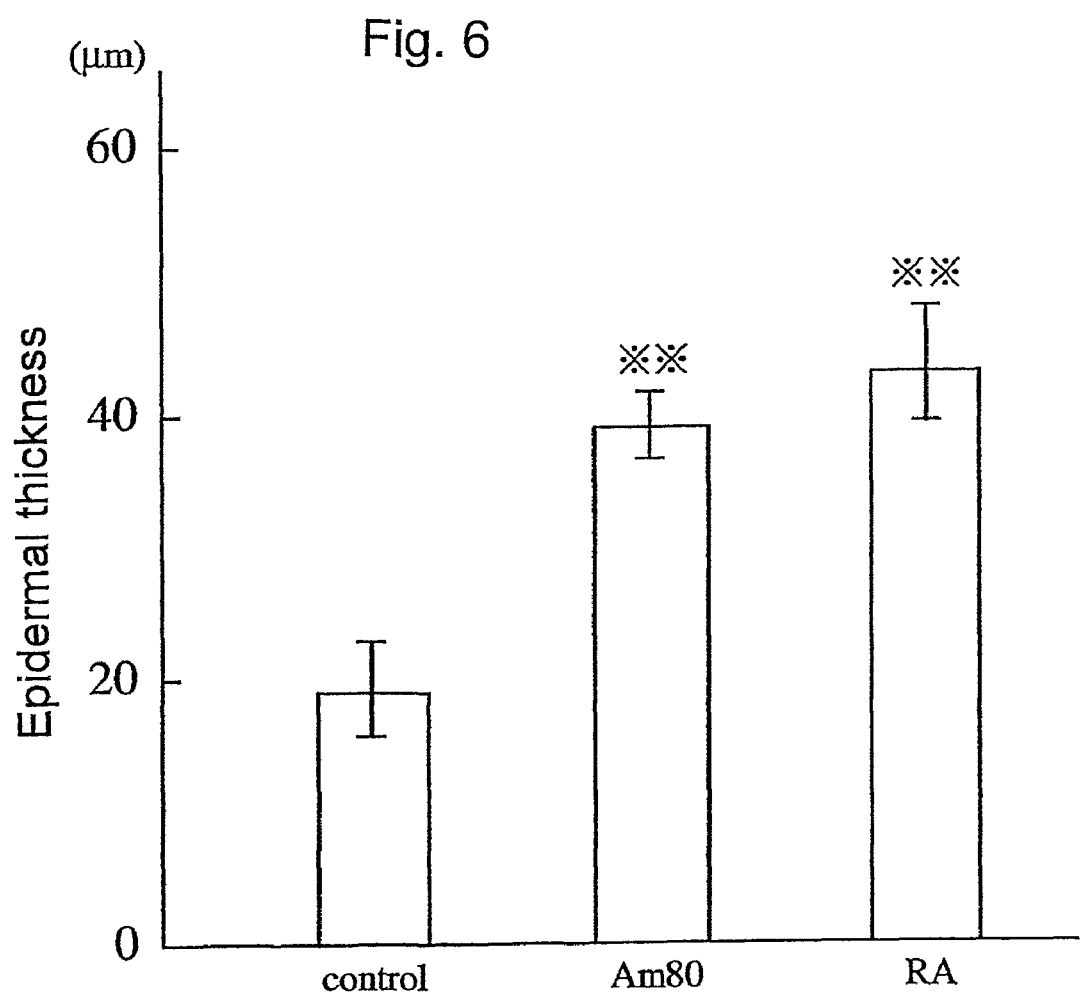

ANTI-WRINKLE AGENT

CROSS-REFERENCE TO RELATED APPLICATIONS

This application is a divisional of application Ser. No. 10/932,097, filed Sep. 2, 2004 now abandoned, which claims priority of Japanese Application No. 2004-068454, filed Mar. 1, 2004, the disclosures of each of these applications are incorporated by reference herein in their entireties.

FIELD OF INVENTION

The present invention relates to an anti-wrinkle agent. More specifically, the present invention relates to a medicament which reduces wrinkles on skin.

BACKGROUND ART

Retinol or retinal has been known to be effective against skin disorders such as wrinkles, warts, eczema, and dandruff (European Published Unexamined Patent Application No. 391033, U.S. Pat. No. 3,932,665, U.S. Pat. No. 4,934,114 and the like). Retinoic acid has been known to reduce wrinkles (European Published Unexamined Patent Application No. 379367, Drugs and Aging, 2, pp. 7-13, 1992). This substance has been used in the United States as a medicament for treatment of skin damaged from ray of sunlight. It is reported that wrinkles caused by aging can be treated with retinal, retinal, and retinoic acid (U.S. Published Unexamined Patent Application No. 2001/53347). However, retinoic acid is highly irritative to skin and induces flare or inflammatory dermatitis. Therefore, development of an anti-wrinkle agent which is low epispastic has been desired.

The term "retinoids" is a general name for compounds which exert similar actions to those of retinoic acid or a part of the actions by binding to receptors that are essential for expression of the physiological actions of all-trans-retinoic acid or 9-cis-retinoic acid (three sub-types of each receptor are known to exist). Among them, some compounds have almost the same level of actions as that of retinoic acid or a higher level of actions. However, a skin irritative action generally increases in proportion to the level of the pharmacological actions (J. Med. Chem., 32, pp. 834-840, 1989). Moreover, 4-[(5,6,7,8-tetrahydro-5,5,8,8-tetramethyl-2-naphthalenyl) carbamoyl]benzoic acid, one of typical retinoids, has been reported to be ineffective on dermatopathy caused by rays of sunlight (WO96/30009).

DISCLOSURE OF THE INVENTION

An object of the present invention is to provide a medicament which reduces wrinkles on skin. More specifically, the object of the present invention is to provide a medicament which has reduced irritation to skin and excellent anti-wrinkle actions.

Through various studies on physiological actions of retinoids, the inventors of the present invention found that a particular class of retinoids have potent anti-wrinkle actions, and further they have much reduced skin irritative action. The present invention was achieved on the basis of these findings.

The present invention thus provides a medicament having an anti-wrinkle action, which comprises as an active ingredient a retinoid having a fundamental structure of a phenyl substituted carbamoyl benzoic acid or a phenyl substituted carboxamide benzoic acid. According to a preferred embodiment of the present invention, provided are the aforementioned medicament wherein the retinoid does not substantially bind to a retinoic acid receptor (RAR) sub-type γ; the aforementioned medicament wherein the retinoid having the fundamental structure of a phenyl substituted carbamoyl benzoic acid or a phenyl substituted carboxamide benzoic acid is 4-(3,5-bis(trimethylsilyl)phenylcarboxamide)benzoic acid or 4-[(5,6,7,8-tetrahydro-5,5,8,8-tetramethyl-2-naphthalenyl)carbamoyl]benzoic acid.

From another aspect, provided are a use of the retinoid having a fundamental structure of a phenyl substituted carbamoyl benzoic acid or a phenyl substituted carboxamide benzoic acid for the manufacture of the aforementioned medicament; and a method for reducing wrinkles on skin which comprises a step of applying to skin the retinoid having a fundamental structure of a phenyl substituted carbamoyl benzoic acid or a phenyl substituted carboxamide benzoic acid.

The medicament of the present invention an excellent anti-wrinkle action, and is characterized to have more reduced skin irritative action than those of conventional medicaments such as retinoic acid.

BRIEF EXPLANATION OF DRAWINGS

FIG. 6 shows degrees of skin thickening by RA and Am80.

BEST MODE FOR CARRYING OUT THE INVENTION

Figure 1:
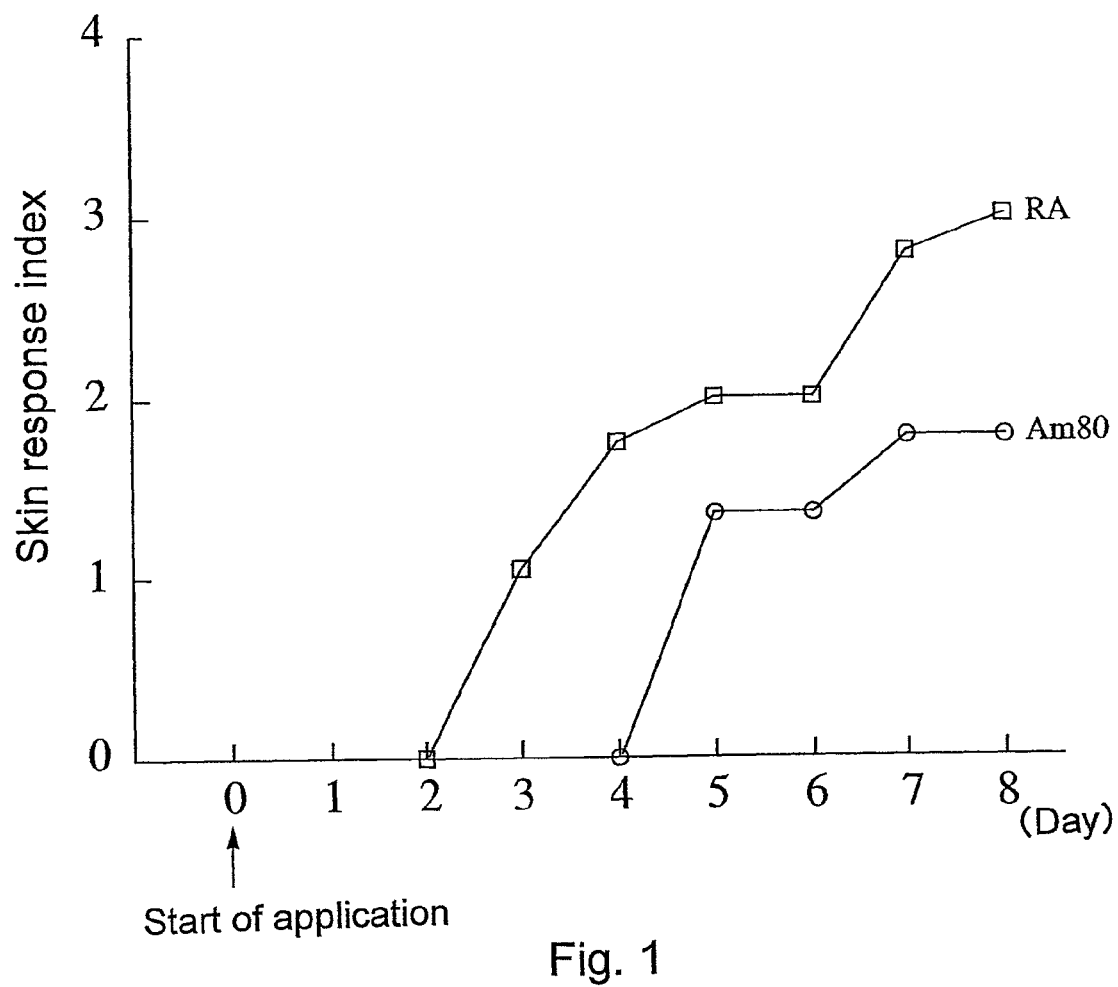
FIG. 1 shows results of cumulative skin irritancy test (50 ppm application) of a retinoid on guinea pig skin (changes with date).

As an active ingredient of the medicament of the present invention, a retinoid having a fundamental structure of a phenyl substituted carbamoyl benzoic acid or a phenyl substituted carboxamide benzoic acid can be used. Varieties of retinoids having a fundamental structure of a phenyl substituted carbamoyl benzoic acid or a phenyl substituted carboxamide benzoic acid are known. The term "fundamental structure" means a main chemical structure to which one or more of any kinds of substituents bind. Generally, the phenyl group which substitutes on a carbamoyl group or a carboxamide group preferably has one or more substituents. As such substituents, for example, a lower alkyl group can be used (in the specification, the term "lower" means about 1 to 6, preferably 1 to 4 carbon atoms). As the lower alkyl group, a linear or branched alkyl group is preferred. More specifically, examples include methyl group, ethyl group, n-propyl group, isopropyl group, n-butyl group, sec-butyl group, and tert-butyl group.

As the substituents of the aforementioned phenyl group, examples include a lower alkoxy group such as methoxy group, a halogen atom (as the halogen atom, any of fluorine, chlorine, bromine, and iodine atom may be used), and a lower alkyl substituted silyl group such as trimethyl silyl group. As the phenyl group substituting on the carbamoyl group, for example, a phenyl group substituted with 2 to 4 lower alkyl groups or a phenyl group substituted with 1 to 2 tri-lower alkyl silyl groups is preferred. A phenyl group substituted with 2 to 4 alkyl groups or a phenyl group substituted with two trimethylsilyl groups is more preferred.

When the two lower alkyl groups substituting on the aforementioned phenyl group are in adjacent positions, the two lower alkyl groups may combine to form one or two, preferably one, 5- or 6-membered ring together with the ring constituting carbon atoms of the phenyl group to which the alkyl groups bind. The ring thus formed may be saturated or unsaturated and may be substituted with one or more lower alkyl groups such as methyl group and ethyl group. The above formed ring may be substituted with preferably two to four, more preferably two methyl groups. For example, two adjacent lower alkyl groups substituting on the phenyl group may preferably combine to form 5,6,7,8-tetrahydronaphthalene ring, 5,5,8,8-tetramethyl-5,6,7,8-tetrahydronaphthalene ring or the like.

In the specification, the term "retinoid" means a class of compounds which exert similar actions to those of retinoic acid or a part of the actions by binding to receptors essential for expression of the physiological actions of all-trans-retinoic acid or 9-cis-retinoic acid, and the term means the above compounds having at least one or more retinoid-like actions such as cell differentiation action, cell proliferation-promoting action, and a life sustaining action. Weather or not a compound is a retinoid can be easily judged by various methods described in M. Sporn et al., Retinoids, Academic Press, 1984. Retinoids generally have a property of binding to a retinoic acid receptor (RAR). Preferably, retinoids used as active ingredients of the medicaments of the present invention are those binds to subtype α (RAR α) and subtype β (RAR β) of the RAR, and does not substantially bind to subtype γ (RAR γ). The bindings to the retinoic acid receptor subtypes can be easily verified by a method described in a publication (H. de The, and A. Dejean, "Retinoids, 10 years on", Basel, Karger, pp. 2-9, 1991).

As a preferred retinoid, an example includes a compound represented by the following general formula (I):

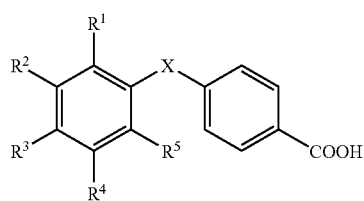

[wherein $R^1$, $R^2$, $R^3$, $R^4$, and $R^5$ each independently represents hydrogen atom, a lower alkyl group, or a lower alkyl substituted silyl group, and when any two adjacent groups of $R^1$, $R^2$, $R^3$, $R^4$, and $R^5$ are lower alkyl groups, the two groups may combine to form a 5- or 6-membered ring together with the carbon atoms on the benzene ring to which the groups bind (said 5- or 6-membered ring may have one or more alkyl groups), and X represents —CONH— or —NHCO—].

In the aforementioned general formula (I), as the lower alkyl group represented by $R^1$, $R^2$, $R^3$, $R^4$, and $R^5$, a linear or branched alkyl group having 1 to 6, preferably 1 to 4, carbon atoms may be used. For example, methyl group, ethyl group, n-propyl group, isopropyl group, n-butyl group, sec-butyl group, or tert-butyl group may be used. On the aforementioned lower alkyl group, one or more of any kinds of substituents may exist. As the substituent, for example, hydroxy group, a lower alkoxy group, and a halogen atom can be exemplified. As the lower alkyl substituted-silyl group represented by $R^1$, $R^2$, $R^3$, $R^4$, and $R^5$, an example includes trimethylsilyl group.

Any two adjacent lower alkyl groups selected from the group consisting of $R^1$, $R^2$, $R^3$, $R^4$, and $R^5$ may combine to form one or two, preferably one, 5- or 6-membered ring together with the carbon atoms on the benzene ring to which the groups bind. The ring thus formed may be saturated, partially saturated, or aromatic, and the ring may have one or more alkyl group. As the alkyl group which may substitute on the ring, a linear or branched alkyl group having 1 to 6, preferably 1 to 4, carbon atoms may be used. For example, methyl group, ethyl group or the like may be used, and the ring may be substituted with preferably 2 to 4, more preferably 4, methyl groups. For example, the benzene ring on which $R^2$ and $R^3$ substitute together with $R^2$ and $R^3$ may preferably form 5,6,7,8-tetrahydronaphthalene ring, 5,5,8,8-tetramethyl-5,6,7,8-tetrahydronaphthalene ring or the like.

More specifically, as a retinoid having a fundamental structure of a phenyl substituted carbamoyl benzoic acid or a phenyl substituted carboxamide benzoic acid used as an active ingredient of the medicament of the present invention, examples include 4-(3,5-bis(trimethylsilyl)phenylcarboxamide) benzoic acid (Am555s, J. Med. Chem., 33, pp. 1430-1437, 1990) and 4-[(5,6,7,8-tetrahydro-5,5,8,8-tetramethyl-2-naphthalenyl)carbamoyl]benzoic acid (Am80, Hashimoto, Y., Cell struct. Funct., 16, pp. 113-123, 1991; Hashimoto, Y., et al., Biochem. Biophys. Res. Commun., 166, pp. 1300-1307, 1990). As the retinoid, a substance in a salt form as well as a compound in a free form can be used. A hydrate or a solvate of the free form or the salt may also be used. Types of the salt are not particularly limited, and for example, sodium salt or the like is preferred. When a retinoid as an active ingredient of the medicament of the present invention has one or more asymmetric carbon atoms depending on types of the substituents, stereoisomers such as optical isomer and diastereoisomer in a pure form, as well as any mixtures of the stereoisomers, racemates or the like may be used as an active ingredient of the medicament of the present invention.

The medicament of the present invention is effective as a medicament used for reducing wrinkles on skin. Causes of wrinkles are not particularly limited. Wrinkles caused by aging are preferable targets of the medicament of the present invention. The medicament of the present invention can apply to wrinkles caused by dermatopathies due to rays of sunlight or drugs, juvenile multi-wrinkle, and the like.

The routes of administration of the medicament of the present invention are not particularly limited. The medicament can be administered orally or parenterally. As the medicament of the present invention, one or more of substances selected from the group consisting of the aforementioned retinoids and salts thereof, and hydrates thereof and solvates thereof. As the medicament of the present invention, the aforementioned substance, per se, may be administered. Preferably, the medicament can be administered as a pharmaceutical composition for oral or parenteral administration which can be prepared by a method well known to one of ordinary skill in the art. As pharmaceutical compositions suitable for oral administration, examples include tablets, capsules, powders, subtle granules, granules, liquids, and syrups. As pharmaceutical compositions suitable for parenteral administration, examples include injections, suppositories, inhalant, eye drops, nasal drops, ointments, creams, and patches. The medicament of the present invention is preferably applied parenterally to skin or mucous membrane as a pharmaceutical composition in a form of an external preparation for topical administration. Types of pharmaceutical compositions in a form of external preparations are not particularly limited. For example, ointment, creams, lotions, and solutions can be exemplified.

The aforementioned pharmaceutical composition can be prepared by addition of physiologically and pharmacologically acceptable additives. As physiologically and pharmacologically acceptable additives, examples include excipients, disintegrants or disintegration aids, binders, lubricants, coating agents, coloring agents, diluting agents, base materials, dissolving agents or dissolving aids, isotonizing agents, pH modifiers, stabilizers, propellants, and adhesives. The pharmaceutical composition in a form of an external preparation can be formulated by using pharmaceutical additives generally used for external preparations and by a method well known to one of ordinary skill in the art. Types of the pharmaceutical additives are not particularly limited. For example, water soluble or oily polymer base materials, surfactants, pH modifiers, buffing agents, isotonizing agents, preservatives, thickeners, organic solvents such as ethanol can be exemplified. Further, amounts of the additives to be mixed are not particularly limited. Suitable amounts can be chosen depending on a type of formulation.

A dose of the medicament of the present invention is not particularly limited. The dose may be suitably increased or decreased depending on various factors which should generally be taken into consideration, such as the body weight and age of a patient, the type and condition of a disease, the administration route, and the like. Generally, the medicament can be used in a range of about 0.01 to 1,000 mg for oral administration per day for an adult, and the aforementioned dose may suitably be increased or decreased. A dose of the medicament in a form of an external preparation is also not particularly limited. For example, the dose is about 1 pg to 1 mg per day as a dose for topical administration. The dose can be suitably increased or decreased depending on conditions and the like.

EXAMPLES

The present invention will be explained more specifically with reference to examples. However, the present invention is not limited to the following examples.

Example 1

Skin Irritancy

Histological tests were conducted to study the irritancy of a retinoid on guinea pig skin and correlation between an irritancy threshold and a retinoid action threshold. Each of male guinea pigs of approximately in a weight of 600 g was applied once every day with 1, 5, 10, 50, or 100 ppm of retinoic acid (RA) or Am80 (4-[(5,6,7,8-tetrahydro-5,5,8,8-tetramethyl-2-naphthalenyl)carbamoyl]benzoic acid) as an ethanol solution on the dorsal skin (5 days a week). As a control, only the solvent (ethanol) was applied. The skin responses were evaluated according to the following 5-step criteria, and average values were calculated for each concentration of the drugs by using results obtained from three of the guinea pigs.
0: No skin response was observed.
1: Slight erythema was observed.
2: Obvious erythema was observed.
3: Strong erythema or slight edema/crust was observed.
4: Obvious edema/crust, or more severe changes was observed.

Figure 2:
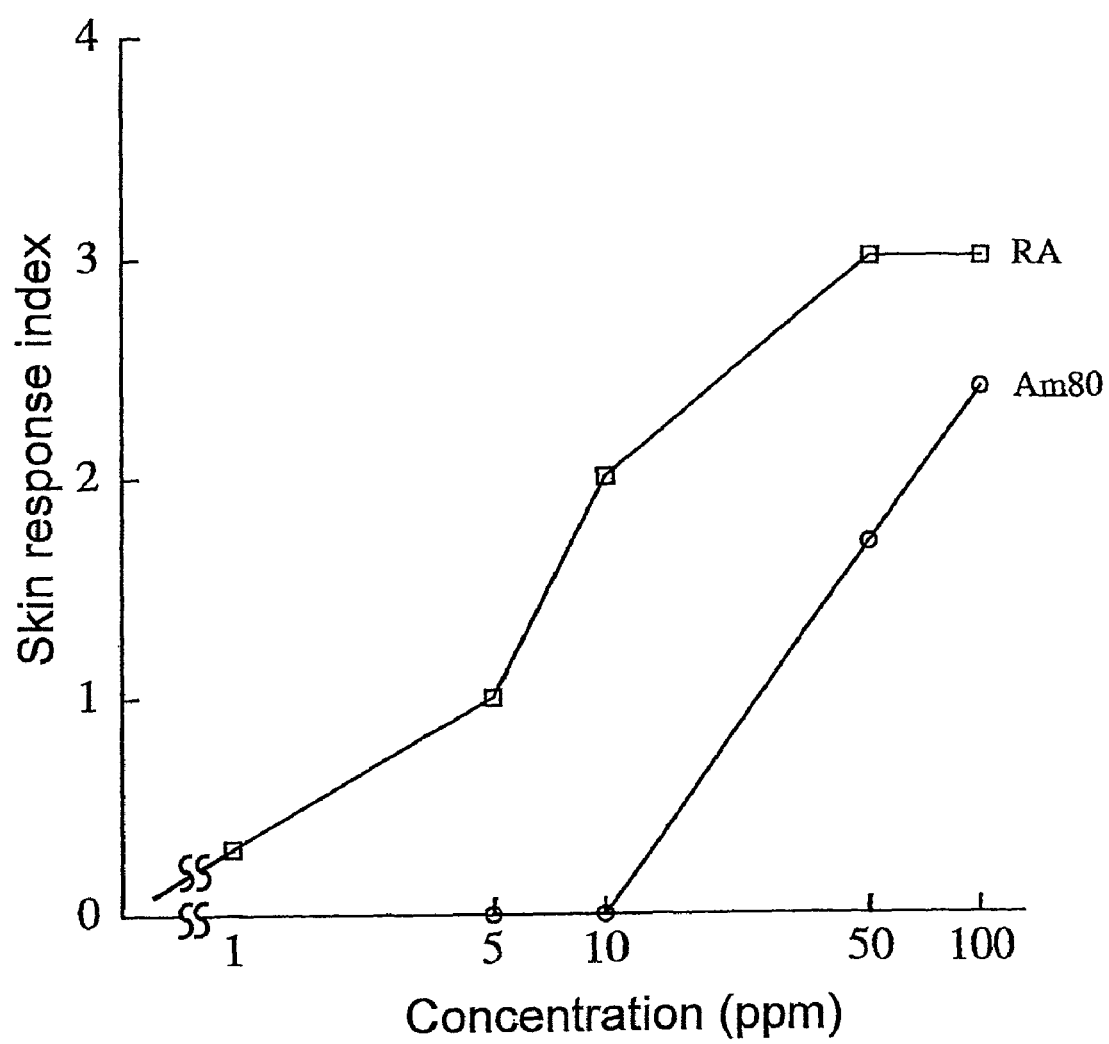
FIG. 2 shows results of cumulative skin irritancy test (50 ppm application) of a retinoid on guinea pig skin (the 9th day of application).

The results are shown in FIG. 1. Comparison of RA and Am80 at the same concentration revealed that Am80 induces much weaker skin response than retinoic acid and induces extremely slow skin response. Further, concentration dependencies of cumulative skin irritancy of RA and Am80 for the same application period were compared. As a result, RA irritancy threshold was less than 5 ppm and the irritancy was increased concentration dependently, whereas Am80 of 10 ppm or less induced no skin responses during this period (FIG. 2). Table 1 shows results of a comparison of histological findings at the end of the application period. As compared with RA, Am80 caused more slight skin thickening and inflammatory changes even when applied at 10 times higher concentration.

TABLE 1

|  | RA | | Am80 | | |
| --- | --- | --- | --- | --- | --- |
| Concentration (ppm) | 1 | 5 | 1 | 10 | 50 |
| Skin Response | − | ± | − | − | ± |
| Epidermis | | | | | |
| Skin thickening | ± | ++ | − | − | + |
| Cell infiltration | − | ± | − | − | − |
| Edema (Intercellular) | − | + | − | − | ± |
| Edema (Intracellular) | ± | + | − | − | ± |
| Dermis | | | | | |
| Cell infiltration | − | + | − | − | ± |
| Vasodilation | − | + | − | − | + |
| Thinning of horny cell layer | − | + | − | − | ± |
| Mucin staining | − | + | − | − | ± |
| (Increase in positive substances between dermis upper layer and basal membrane) | | | | | |
| Application period | 20 days | | 20 days | | |

Example 2

Horny Layer Turnover Test

Figure 3:
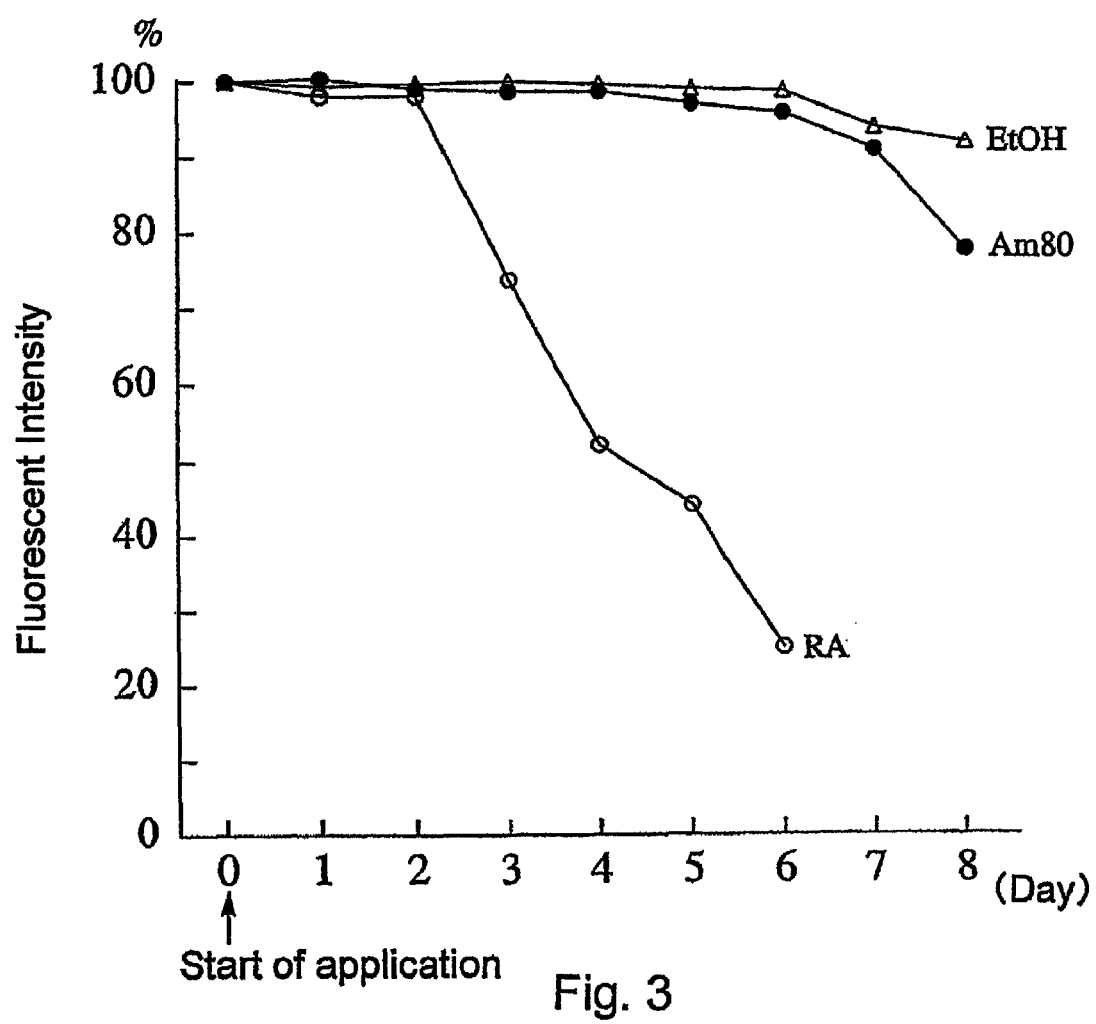
FIG. 3 shows results of the horny layer turnover test.
Figure 4:
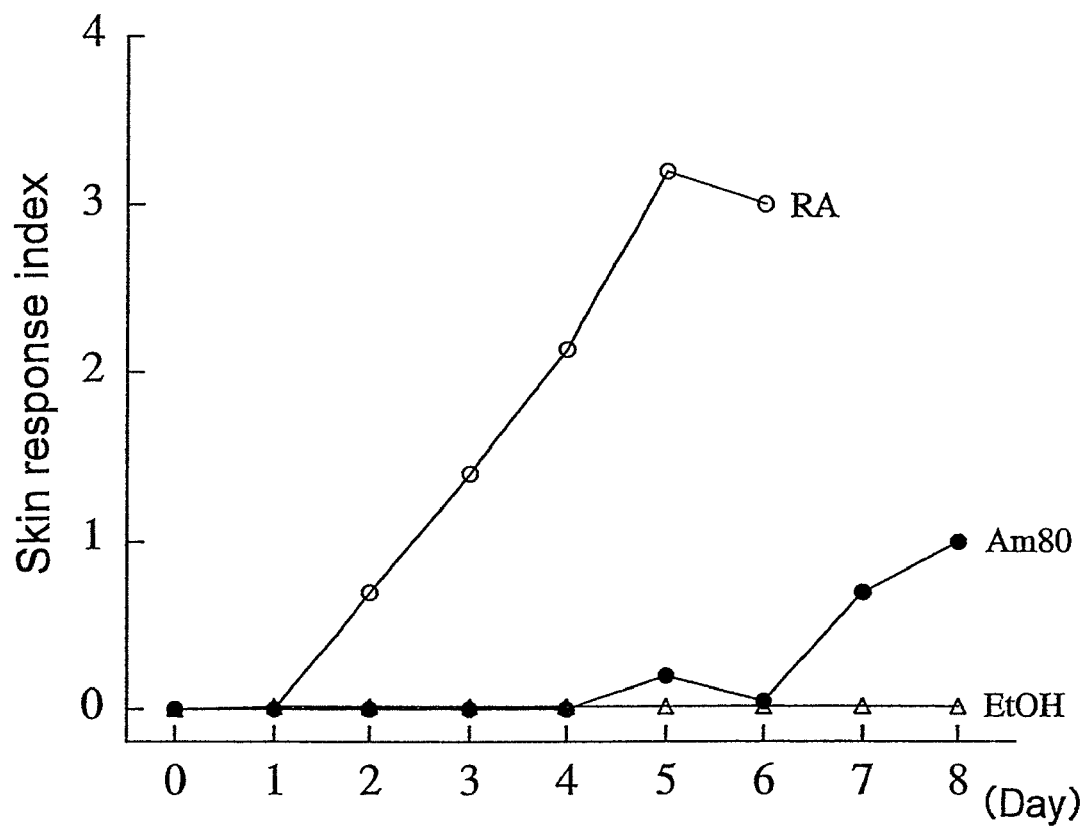
FIG. 4 shows results of cumulative skin irritancy in the horny layer turnover test.

Actions on turnover of horny layer were evaluated by using guinea pigs. Hartley albino male guinea pigs of approximately 750 g in weight, whose hair was removed using depilatory wax three days prior to the experiment, were applied occlusively with 5% Vaseline ointment of dansylchloride for 24 hours using a patch test Finn Chamber, and then the skin of the guinea pigs were wiped to remove the ointment. A portable fluorometer was used for irradiation with ultraviolet rays having maximum at around 338 nm, and the fluorescent intensity of the dansylchloride was measured. Simultaneously, fluorescent intensity of an area where dansylchloride was not applied (blank value) was measured in the same manner. After the measurement of the fluorescent intensities, 10 μl/1 cm diameter of RA and Am80 at 50 ppm concentration were applied once a day. During the measurement, skin irritancy was also determined according to the criteria indicated in Example 1. The results of the horny layer turnover test are shown in FIG. 3. It was revealed that RA has strong accelerating action on the horny cell layer turnover, whereas Am80 has almost no effect on the horny cell layer turnover. Cumulative skin irritancy was simultaneously evaluated according to the criteria in Example 1, and the results were obtained as shown in FIG. 4.

Example 3

Planarization Action on Skin Surface Formation (Skin Groove)

Figure 5:
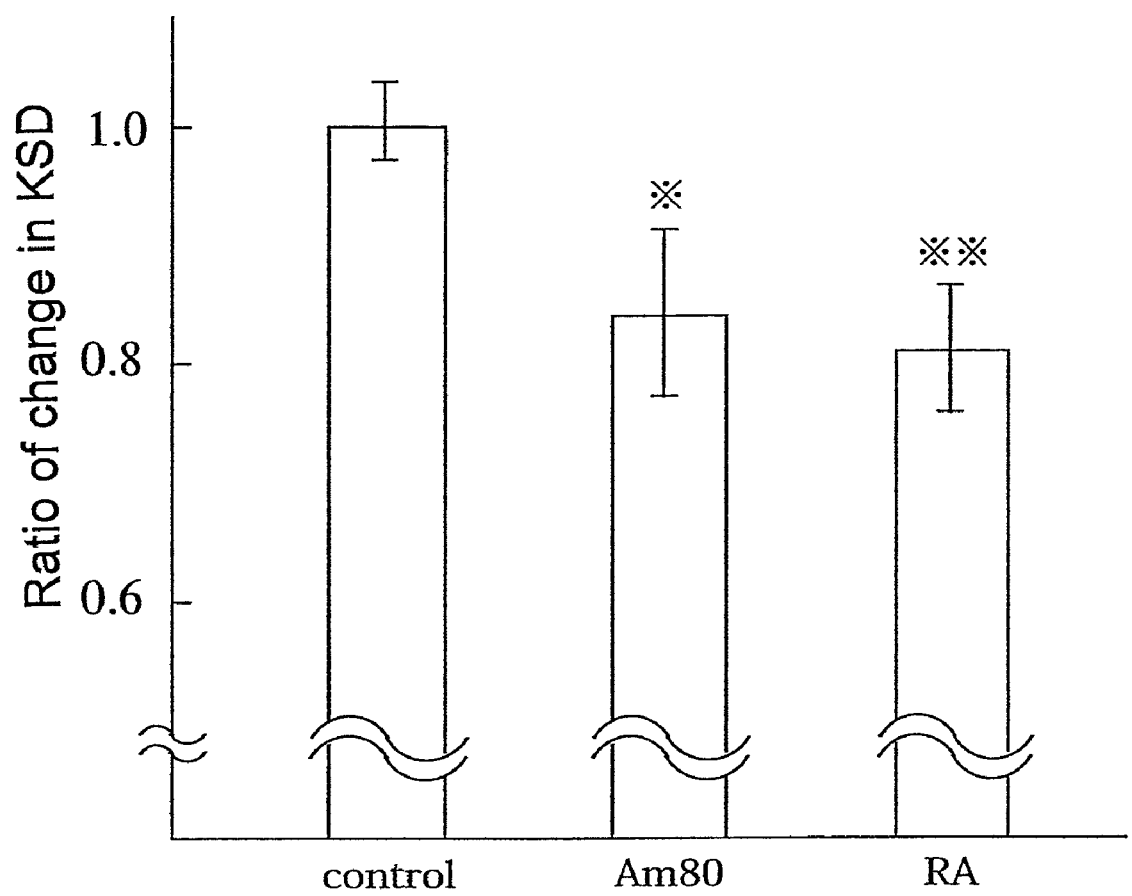
FIG. 5 shows results of determination for RA and Am80 of parameter KSD which correlates to the depth of skin grooves.

Changes which appear on skin grooves after applications of RA and Am80 (each at a concentration of 0.01% in ethanol)

were studied by using hairless mice (Skh-h4l, 16 weeks old, female, 5 mice per group). The applications were conducted once a day, 5 days a week, and for 30 days. As a control, only ethanol was applied. On the next day of the day of last application, replicas of skin surfaces were created by using a silicon resin, and various parameters that represent features of the shape of the skin surface were determined by using an apparatus for image analysis. As a result, dermatography on the replicas were disappeared by the repeated application of RA, and planarization changes of the surfaces were observed. The same action was observed for Am80. The image analysis parameter KSD (the dispersion of luminance distribution in a 3.9 mm×3.9 mm pixel), which correlates to the depth of skin grooves, was significantly decreased in the drug applied group (FIG. 5). Further, the decrease in KSD correlated to epidermal thickening. Both of Am80 and RA gave obvious changes (FIG. 6).

Example 4

Actions of Fibroblast cells on EGF-Dependent Growth

The growth of fibroblast cells, being suspended under a low serum level, is dependent on growth factors, and the growth will start by the addition of EGF. The acceleration effects of RA and Am80 on the EGF-dependent growth were evaluated. RA gave the maximum effect (40% promotion) at $10^{-6}$ M, and Am80 gave the maximum effect (30% promotion) at $10^{-8}$ M. The acceleration effect of Am80 (10%) was also observed at $10^{-10}$ Ml.

Example 5

Actions on Human Keratinocyte Growth and Differentiation

Normal human keratinocyte obtained from human chest skin (HK, Kurabo) was cultured, and the cells were added with RA or Am80 (0.01% in dimethyl sulfoxide) on the second day. The cells on the second to $13^{th}$ day after the addition of the agents were used as samples. By using the amount of DNA as an index of HK growth, and by using compositional ratio (K1/K16) of differentiated keratin (k1; 68 kD) and proliferating keratin (K16; 48 kD) in one-dimension SDS-PAGE as an index of differentiation, differentiation suppression rate was determined as a value wherein the ratio of the indexes of each sample and control applied only with a solvent was subtracted from 1. Am80 has a similar cell growth suppression action to that of RA. $IC_{50}$ was $10^{-6}$ to $10^{-7}$ M for RA, and $10^{-9}$ M for Am80. In addition, a cell differentiation suppression action of Am80 is stronger than that of RA, and also observed at a concentration as low as $10^{-8}$ to $10^{-10}$ M, and the suppression rates by Am80 were 1.3 to 1.7 times as compared to that by RA.

The present disclosure relates to subject matter contained in Japanese Patent Application No. 2004-068454, filed on Mar. 11, 2004, the contents of which are herein expressly incorporated by reference in its entirety.

What is claimed is:

1. A method for decreasing depth of grooves of wrinkles on skin, the wrinkles being caused by dermatopathies due to rays of sunlight, which comprises applying to the wrinkles on the skin caused by dermatopathies due to rays of sunlight only one retinoid as an active ingredient in an amount effective to decrease depth of grooves of the wrinkles, wherein the retinoid is 4-(3,5-bis(trimethylsilyl) phenylcarboxamide) benzoic acid.

2. A method for decreasing depth of grooves of wrinkles on skin, the wrinkles being caused by dermatopathies due to rays of sunlight, which comprises applying to the wrinkles on the skin caused by dermatopathies due to rays of sunlight only one retinoid as an active ingredient in an amount effective to decrease depth of grooves of the wrinkles, wherein the retinoid is 4-[(5,6,7,8-tetrahydro-5,5,8,8-tetramethyl-2-naphthalenyl)carbamoyl]benzoic acid.

* * * * *